United States Patent [19]

Doherty et al.

[11] 4,165,739

[45] Aug. 28, 1979

[54] INOCULATOR

[76] Inventors: Norman R. Doherty, 870 Main St., Farmingdale, N.Y. 11735; Richard F. Doherty, 2 Freshman La., Stony Brook, N.Y. 11790

[21] Appl. No.: 790,239

[22] Filed: Apr. 25, 1977

Related U.S. Application Data

[63] Continuation-in-part of Ser. No. 719,733, Sep. 2, 1976, Pat. No. 4,090,512.

[51] Int. Cl.² ............................................. A61M 31/00
[52] U.S. Cl. ................................................. 128/173 H
[58] Field of Search ........... 128/173 H, 173 R, 220 R, 128/218 F, 218 G, 218 A, 215 R, 216 R

[56] References Cited

U.S. PATENT DOCUMENTS

| | | | |
|---|---|---|---|
| 2,490,553 | 12/1949 | Smith | 128/220 |
| 2,717,597 | 9/1955 | Hein, Jr. | 128/173 H |
| 2,821,981 | 2/1958 | Ziherl et al. | 128/173 H |
| 3,425,413 | 2/1969 | Stephens | 128/173 H |
| 3,461,867 | 8/1969 | Zimmet et al. | 128/173 H |
| 3,507,276 | 4/1970 | Burgess | 128/173 R |
| 3,815,594 | 6/1974 | Doherty | 128/173 H |

*Primary Examiner*—Henry J. Recla

[57] ABSTRACT

An inoculator for injecting a fluid through the skin without the use of a needle and in which an ampule of the fluid is replaceably positioned to dispense the required dosage to and from a selected ejector head that receives the dose under predetermined pressure in response to the release of stored energy.

8 Claims, 9 Drawing Figures

FIG.3 PART TWO (DISCHARGED)

FIG.5

INOCULATOR

CROSS REFERENCE TO RELATED APPLICATION

This application is a continuation-in-part of co-pending U.S. patent application Ser. No. 719,733, filed Sept. 2, 1976 now U.S. Pat. No. 4,090,512.

FIELD OF THE INVENTION

The present invention relates to an inoculator and, more particularly, to an inoculator in which the same automatically, completely and fully purges itself of air during each separate loading of the inoculator with the inoculating serum.

BACKGROUND OF THE INVENTION

The invention relates to fluid injectors and more particularly, to inoculators for injecting fluids into the body without the use of a needle and without the attendant tearing or abrasion of the skin.

Prior art devices for performing the purposes of the present invention but utilizing different structures have been disclosed in the U.S. Pat. No. 3,461,867 to Zimmet et al.

A similar disclosure is contained in prior U.S. Pat. No. 3,815,594.

SUMMARY OF THE INVENTION

The desideratum of the invention is to provide an inoculator that is simple in construction so as to enable the same to be manufactured quickly, easily and relatively inexpensively with the least possible moving parts that are able to be assembled readily and positively.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings.

DESCRIPTION OF THE DRAWINGS

In the drawings, in which like reference characters designate like parts.

DESCRIPTION OF THE INVENTION

The injector, and more particularly, the inoculator apparatus is generally identified by the numeral 10 and includes an overall covering unitary housing or main body 12 that is of one-piece, unitary construction. The housing 12 provides the manipulative support by which the operator is intended to utilize the inoculator 10. The forward or inoculating end of the housing 12 is provided with an interior thread 14 that threadedly supports a sleeve or cylinder 16, the interior of which is hollow and smooth to receive a piston 18 that is adapted to reciprocate axially therein.

The piston 18 is provided with a plurality of piston rings 20, preferably made from a material having high lubricity, as Teflon and the like, to assure a smooth reciprocating motion of the piston 18 within the cylinder sleeve 16. The interior of the piston is provided with a hollow passage 22 that communicates with a valve chamber 24 in which there is mounted a displaceable valve means 26 that is normally urged to the right of the chamber 24 by a valve spring 28. The valve spring 28 acts upon the valve 26 to normally urge the same to close a further inlet passage 30 that communicates with a vial or ampule piercing needle 32.

The piston 18 is provided with an end closure 34 which contains the needle 32 and the passage 30 therein and which end closure is threadily secured within the back end of the piston 18. The connection between the end closure 34 and the piston 18 is made fluid tight by the inclusion of a fluid type seal ring 36 contained within the end closure member 34. The right hand end 38 of the end closure 34 functions as a seat and a rest against which a serum containing ampule, generally identified by numeral 40, may be supported.

In practice, it is immaterial as to the precise structural configuration of the ampule 40; however, generally the ampule 40 is provided with an elongated glass body 42 that is closed at its right hand end by a movable wall 44 an at its left hand end by a metallic cap 46, having a rubber or other puncturable material 48 contained therewithin to retain the contents in a sterile condition. The piston 18 is threadedly joined to a main shaft 50 as at 52, for conjoint reciprocal movement within the main body 12. For this reason, the main body 12 is provided with a conformingly formed interior opening 54 to guide the movement of the main shaft 50 therein.

The main shaft 50 extends axially within the main body 12 for substantially the full length thereof and beyond the right hand end thereof as shown in the drawing. Intermediate its ends it includes a shoulder 56 against one side of which a sear block 58, preferably made of hardened steel material, is mounted. The sear block 58 is ring-shaped in construction to be supported on an enlarged annular seat 60 of the main shaft. It is made of hardened material and preferably of hardened steel to absorb the wear placed upon it by its engagement with, and, at the notch shaped end 62 of a trigger 64 that is pivotally mounted on a pin 66. Pin 66 passes through a pair of spaced ears 68, defined by a slot 69 in the main body 12. The trigger 64 is normally biased into its engaging position, as shown in the drawing, for engagement with the sear block 58 in response to the urging of a yieldable means or spring 70.

Supported in position about the exterior of the main shaft 50 and on the opposite side of the shoulder 56 is an energy storing means, shown here as a main drive spring 72. The main drive spring 72 is retained against the shoulder 56 by a retainer 74 that is slidable along and relative to the main shaft 50; retainer 74 is held, in turn, by a "C" shaped releasable ring 76 mounted within a conforming undercut defined in the interior surface of the main body 12.

Because the main shaft 50 and its attendant structure, described above, slides reciprocably and is guided by such reciprocating movement in the main body 12, such body is provided with an elongated guide opening 77. The main spring 72 may be made of square shaped convolutions; however, any other desired shape or spring material may be utilized. It will be recognized that the shape of the main drive spring 72 is tapered from its right hand end adjacent the retainer 74 downward toward its left hand end adjacent the shoulder 56.

The taper or slope of the spring 72 is deliberately provided to assure a controlled release of stored energy by the spring and a predetermined movement of the main shaft 50 during the performance of the inoculating function, and the ejection of the inoculating serum previously received from the ampule 40 in a manner to be described hereinafter. By using a square shaped spring, the forces to be exerted and released thereby can be predetermined and calculated throughout its length. Thereafter, by grinding down certain turns or windings of the spring 72, the stored forces to be exerted and released over the length of the spring may also be precalculated and predetermined.

Mounted on the right hand threaded end of the main shaft 50 is an interiorly threaded cocking barrel 78 that extends beyond the right hand end of the main shaft 50. The outer right hand extension of the cocking barrel 78 is provided with an annular outer surface 80 that terminates in an upwardly curved abutment wall 82 that is adapted to engage, or be engaged by, a plurality of abuting cocking balls 84 that are mounted in angularly spaced relationship about the circumference of a cocking of resetting member 86. The balls 84 are held in the member 86 for smooth, ball-bearing type sliding engagement with the surface 80 during the cocking or loading action of the inoculator 10 in a manner to be described.

The cocking or resetting or loading member 86 is provided with a series of spur shaped gear teeth 88 formed as a gear rack for engagement with a fixed spur gear 90 that is mounted within a loading housing 92, which loading housing pivots at the axis 94 about supporting base 96. The opposite end of the cocking barrel 78 is threaded at its exterior for threaded adjustable engagement by a dosage adjustment barrel 98. As seen in the drawing, the left hand interior end of the barrel 98 is threaded to the barrel 78 while the right hand interior portion of the barrel 98 is relatively smooth for free movement axially along and relative to the barrel 78 therewithin. The main body 12 is provided with an interior smooth recessed opening 100 to accommodate the axial movement of the dosage barrel 98 and the cocking barrel 78 therewithin.

The interior of the main shaft 50 is essentially hollow and receives for relative sliding movement therein an ampule drive body 102 that is substantially elongated in length and terminates in a threaded exterior at its right hand end for threaded engagement by a drive body cap 104 thereabout. The cap 104 may be made of hardened material to absorb forces supplied to the same during the cocking or loading of the inoculator 10.

The ampule drive body 102 is provided with a bayonet type mounting pin 106 that is fixed thereto and adapted to be releasably engaged within a bayonet type socket or opening 108 that is defined in the circular wall of the main shaft 50. Adjacent to the right hand end of such main shaft, the cooperation between the pin 106 and the socket 108 facilitates the disassembly and assembly of the ampule drive body 102 with the main shaft 50.

To facilitate the aforementioned relative engagement and disengagement, there is provided within the ampule drive body 102 a piston drive spring 110 that is supported and guided in its supported position within the ampule drive body 102 by a guide rod 112 mounted on the interior of the drive body cap 104. The spring 110 abuts the right hand end of the ampule drive piston 114 that is threaded at its right hand exterior end 116 for engagement with the interior of a sleeve shaped ampule pusher tube 118. The ampule pusher tube 118 supports the drive piston 114 for movement within and relative to the ampule drive body 102.

The loading housing 92 has an extension 120 that projects axially to the left thereof to encompass the cocking balls 84, thereby holding the same at the exterior thereof to prevent their accidental displacement from the cocking or loading member 86 radially outward therefrom. At the same time, the holes 122, within which each of the cocking balls 84 seats, are narrowed at their radial inner ends to prevent the balls 84 from falling radially inward and out from their respective holes.

Thus, the balls 84 are retained within the mmeber 86 and from falling radially inward out of the respective holes 122 by the narrowed end of the holes, which are smaller in diameter than the balls. They are restricted from moving radially outward of their respective holes by the extension 120 encompassing the same. The extension 120 is provided with a radially inwardly directed shoulder 124 adjacent to an enlarged recess 126. The axial left hand end of the extension 120 is provided with a pilot slot 128 for the reception of a pilot button 130.

Mounted on the left hand end of the main body 12 of the inoculator 10 is the inoculator or injector head, generally identified by the numeral 132 and shown in detail in FIG. 6A. The head 132 includes an angled extension 134 having an interior thread that is adapted to thread over and about the left hand threaded end 14 of the cylinder 16. The connection between the extension 134 and the cylinder 16 is completed by a seal ring 136 to provide a fluid tight joint therebetween while the extension 134 abuts against the facing end of the main body 12. Defined within the extension 134 is a fluid passage 138 that communicates with the interior serum chamber 140, defined by the interior of the cylinder 16. The head 132 includes an injector body 142 that extends outward from the head 132 and is sealed fluid tightly therewith at a seal 144.

Mounted within the injector body 142 is an outlet orifice member 146 having an orifice 148 of predetermined configuration and size to produce the desired spray or array of inoculating serum to be dispensed by the inoculator 10. A seat 150, having an opening therein coinciding with the orifice 148, is mounted against the interior of the orifice within the body 142 and supports a slidable reciprocating valve 152, which is normally urged downward against the seat 150 by a closure spring 154. The closure spring is mounted within an adjusting head 156 that is threadedly engaged within the upper end of the extension 134 against a seal ring 158 to form a fluid tight closure between the body 142, the extension 134 and the head 156. Thus, for all intents and purposes, the injector or inoculator head 132 is a closed, fluid tight, sealed structure.

The spring 154 may apply variable tension or force to the valve 152 as a result of the adjustment of a threaded member 160, rotatable within the interior threaded surface of the head 156. An additional seal ring 162 may be provided in the body 142 to more fully assure a fluid tight head. Defined within the head 132 is an annular recess which contains an annular filter 164 positioned between the passage 138 and a plurality of communicating passages 166.

In operation, the inoculator 10 is initially loaded with an ampule 40. To accomplish this, the inoculator is removed from the housing 92 and its attendant spring loading structure, as is more fully disclosed in applicant's co-pending application Ser. No. 719,733, which structure forms no part of the present invention. However, for convenience of explanation, the inoculator 10, when it is removed from the loading device, is loaded with an ampule 40 by rotating the drive body cap 104 and its attached ampule drive body 102 relative to the main shaft 50 so as to cause the bayonet engaging pin 106 to disengage from the bayonet socket 108, thereby releasing the ampule drive body from its engagement with the main shaft 50. The ampule drive body 102 is now slid downwardly from the interior of the main shaft 50 aided by the expansion of the piston drive spring 110.

The drive piston 114, its connected ampule pusher sleeve 118, the ampule drive body 102 and the spring 110 are all physically removed from the main shaft 50, leaving the interior thereof hollow and open. A suitable ampule 40 containing the desired inoculator serum is then dropped into the main shaft 50 with the metal cap 46 and the rubber closure or stopper 48 positioned facing the needle 32. The drive piston 114 is then inserted back into the main shaft 50 along with its attendant tube 118, spring 110, and body 102 and, by rotating the cap 104, the pin 106 is once again re-engaged with the bayonet socket 108 to lock and secure all the parts together.

The inoculator 10 is now ready for the dispensing of the serum from the ampule 40. During the reapplication of the drive piston 114 back into the main shaft 50 and the locking engagement of the pin 106 with the socket 108, the ampule cap 46 and closure 48 are pressed against the needle point 32 and move therealong such that the needle penetrates both such members and enters into the interior of the ampule 40. In such relationship, the inoculator 10 is now ready to load the serum by causing the serum to flow from the ampule 40 into the ejecting portions of the inoculator, namely, into the chamber 140 and the injector head 132.

The loading of the inoculator 10 is accomplished in the manner disclosed in the co-pending application Ser. No. 719,733. That is to say, the housing 92 and its attendant extension 120 are placed in a substantially vertical position relative to the base 96. The cocking balls 84 are then located and retained within the confines of the recess 126 thereby enabling the insertion of the cocking barrel 78 between the circumferentially spaced balls so that the balls are able to ride along the surface 80 of the cocking barrel 78.

The drive body cap 104 abuts a clearance opening 170 of the resetting member 86. The inoculator 10 is now in position to be loaded by and within the housing 92. The inoculator 10 is grasped about the main body 12 and rotated downward, using it in the manner of a lever. As the body 12 is rotated downward, it causes the housing 92 and its attendant structure to rotate about the axis 94 and relatively downward towards its horizontal position with respect to the base 96.

During this motion, because the spur gear 90 is fixed in position, the rack 88 is moved to the right and pulled into the housing 92. The rightward pulling movement of the cocking member 86 causes the balls 84 to engage the curved abutment wall 82 on the cocking barrel 78 causing it to similarly move to the right. This rightward movement is transmitted undiminished to the main shaft 50 and also to the piston 18, thereby drawing the piston 18 to the right within the cylinder 16 and enlarging the serum chamber 140.

At the same time, the lower or right hand end of the main body 12 abuts against the facing wall of the shoulder 124 and is, therefore, prevented from any movement relative to the housing 92. As a consequence, the main shaft 50 and the aforedescribed moving structure all move relative to the main body 12.

The rightward movement of the main shaft 50 is also transmitted directly to the ampule drive body 102 and attached body cap 104 through the mutual engagement of the bayonet mounting pin 106 and the bayonet socket 108. The force of compressed piston drive spring 110 on drive piston 114, however, permits ampule pusher 118 to slide within moving ampule drive body 102 to maintain its position relative to main body 12 so that as the serum ampule 40 is forced rightward by end closure member 34, ampule wall 44 is forced further into the ampule 40, thereby driving serum therein outward through hollow needle 32 and connected passage 30, unseating valve 26, and forcing the serum through passage 22 into expanding serum chamber 140 to completely fill the same.

When the serum is driven from the ampule 40 by the drive piston 114, the main shaft 50 is moved to the right with the cocking member 86. This causes the sear block 58 to move to the right with the main shaft 50, sliding along the locking finger of the trigger 64 toward and beyond the notched locking end 62 of the trigger. The rightward cocking or loading motion of the main shaft 50 beyond the trigger locking notch 62 is deliberately performed to effect a movement that causes the sear block 58 to move a distance over and beyond the locking notched end 62. The trigger end 62 must be long enough to accommodate the overtravel of the sear block 58 so the trigger does not fall into the path of the sear block during the charging operation.

This deliberate overmovement of the sear block 58 beyond the notched end 62 is performed in an attempt to fully purge the inoculator of any air that might tend to remain therein. When the inoculator loading housing 92 has reached the limit of its downward changing movement and the downwardly directed force on the housing is released therefrom, the same moves upward a small amount under the force of main drive spring 72 which, by contact with shoulder 56, forces main shaft 50 leftward to engagement of trigger notched end 62 with sear block 58, thereby preparing the inoculator 10 for ejection of serum. This slight leftward movement of the main shaft 50 is transmitted to the piston 18, compressing the serum in chamber 140 and forcing an amount of the same through passage 138 and into the injector head 132. As serum enters the injector head 132, air contained therein will be purged through the orifice 148 as the valve 152 is lifted from its seat in a manner to be described hereinafter.

Figures 3, 6A, 6B:
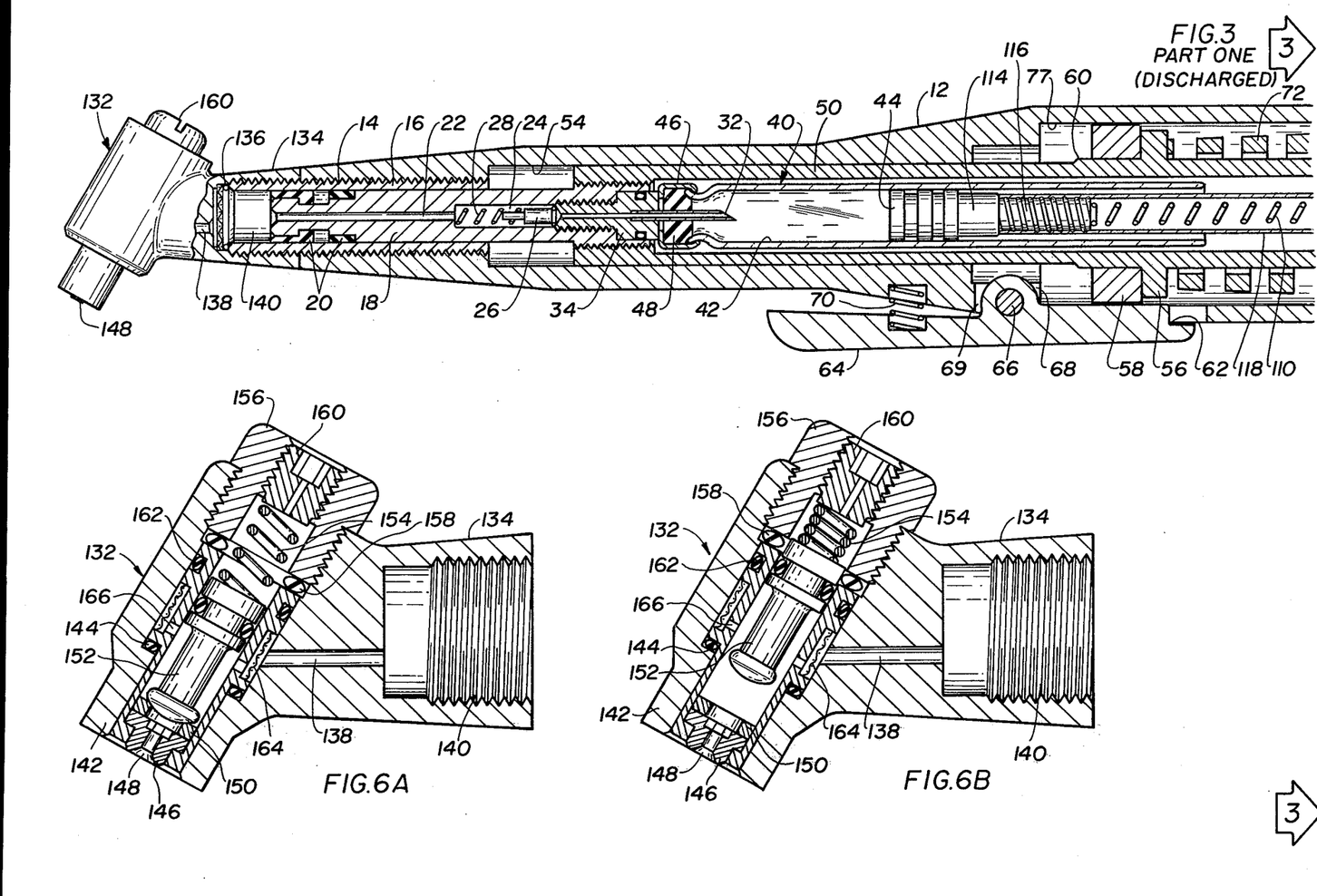
FIG. 3 is an enlarged longitudinal, cross-sectional view of the inoculator in the discharged mode shown on two sheets of drawing.
FIG. 6A is an enlarged cross-sectional view of the injector head of the inoculator in its normal condition.
FIG. 6B is a cross-sectional view similar to FIG. 6A of the injector head in its operative condition discharging liquid.
Figure 3:
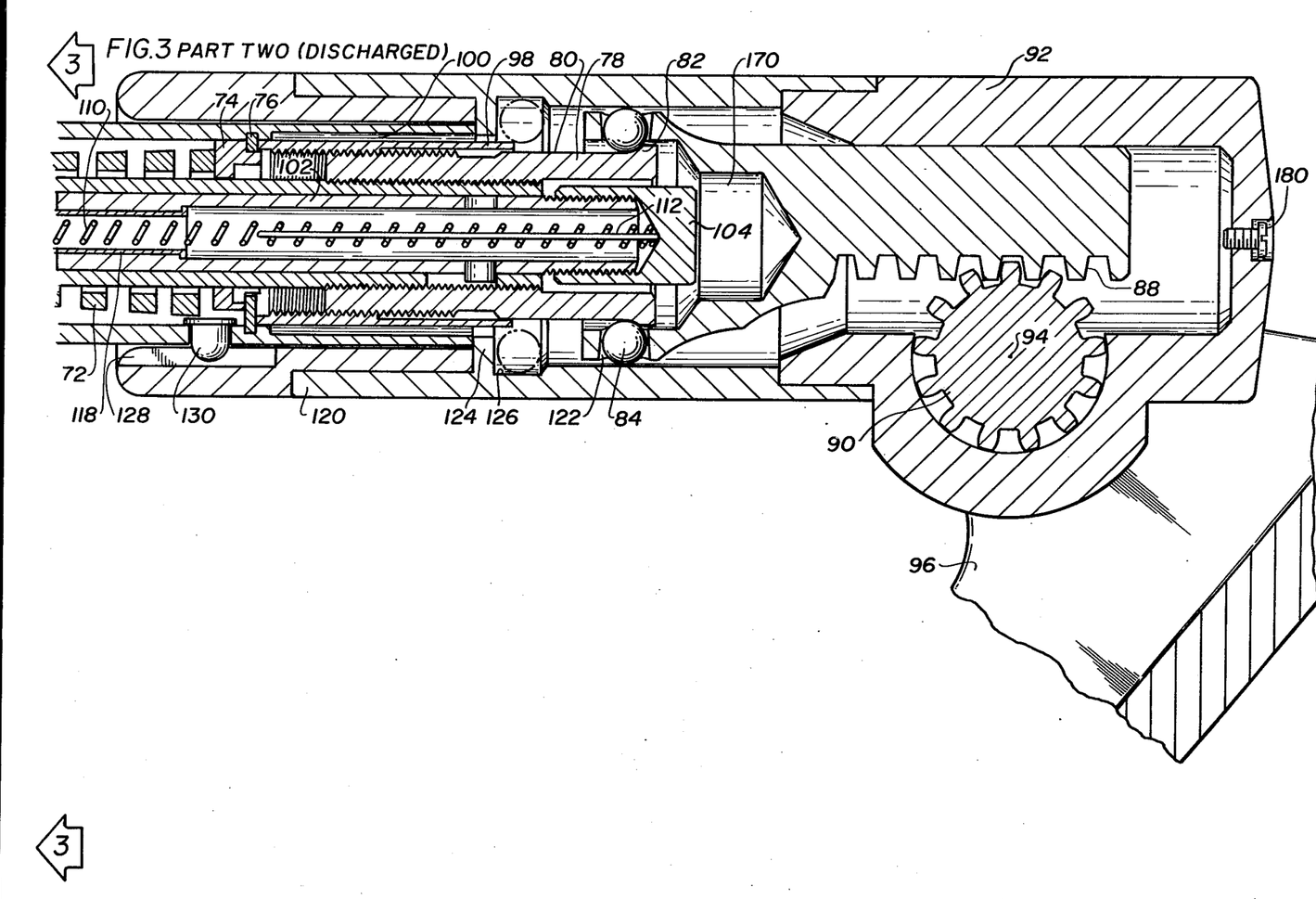
Figure 4:
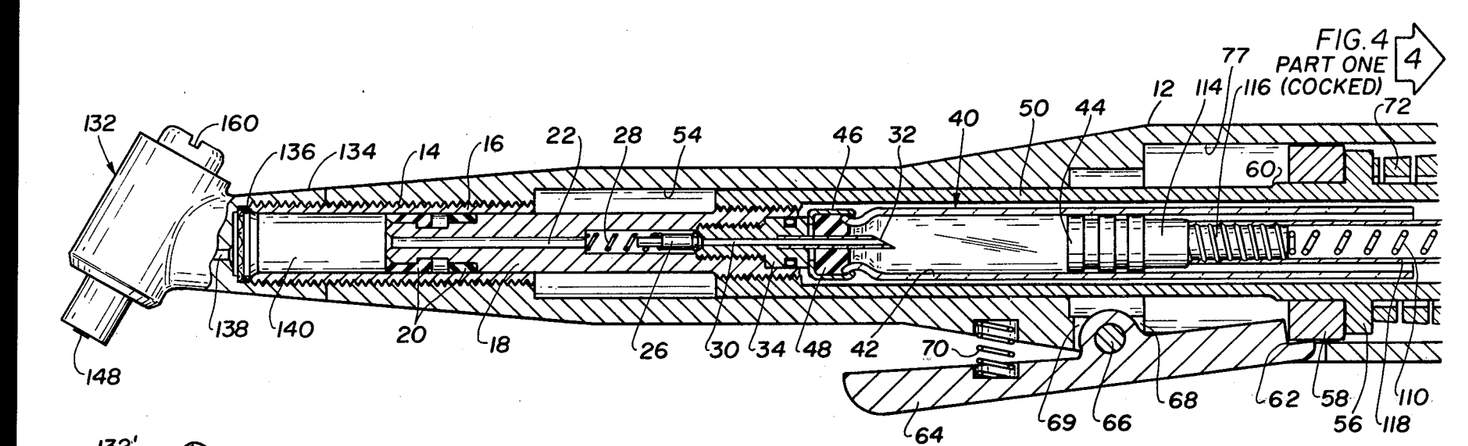
FIG. 4 is an enlarged longitudinal, cross-sectional view similar to FIG. 3 of the inoculator in the corked or charged mode or condition shown on two sheets of drawing.
Figure 5:
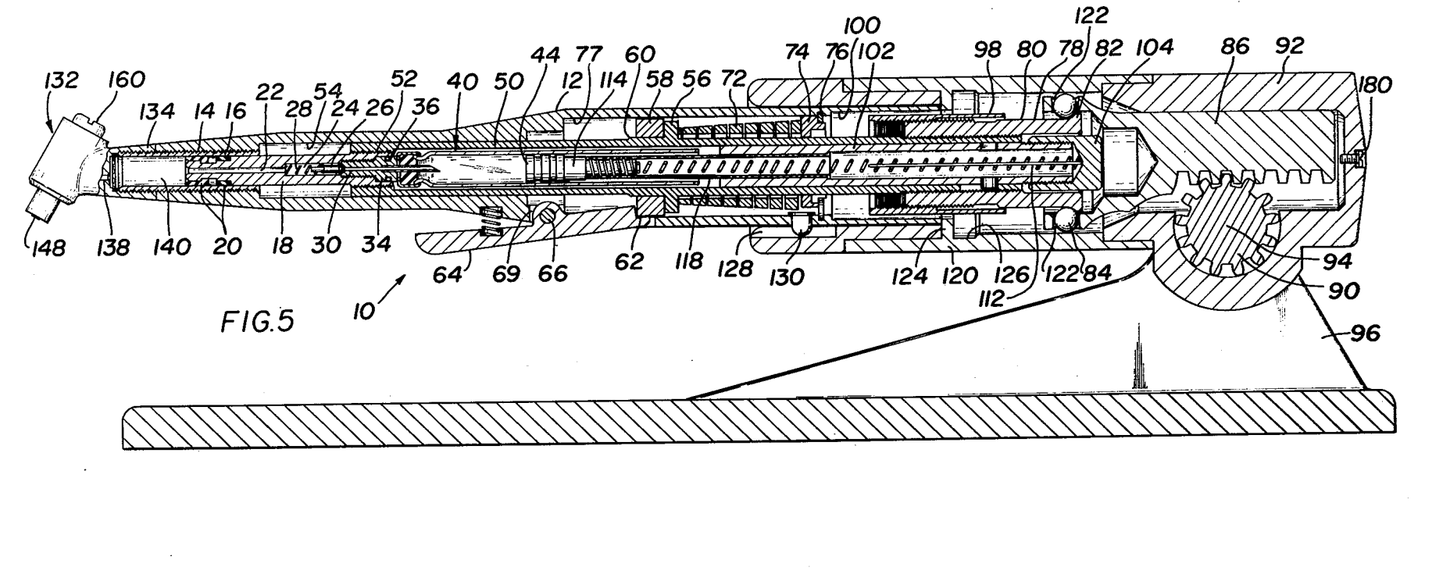
FIG. 5 is a cross-sectional view of the inoculator in the charged or corked condition or mode taken along the length thereof shown in one drawing.

An opening 170 in cocking member 86 provides a clearance for the drive body cap 104 in its rightward movement during the cocking operation. The provision of an adjustable member 180 in the locking housing 92, as shown in FIG. 3, enables adjustment of the member 180 so that the cocking member 86 is restricted in its charging movement to the right thereby acting as a stop to limit the extent of the purging of the ejector head 132 and the serum chamber 140, and positively avoiding the fall of the trigger end 62 into the path of the sear block 58 during the downward charging movement of the loading housing 92. Member 180 is shown in FIG. 3 as an adjustable screw extending through the rear wall of loading housing 92. In an alternative embodiment adjustable vertical member 182 projects from base 96 of the loading device. As shown in FIG. 4, it could be located to contact extension 120 and limit the same in its downward charging movement to accomplish the same result as adjustable member 180.

During the first few operations of the inoculator 10, it is important to assure that the same is completely purged of air. Otherwise, when the inoculator is operated, it is possible that a quantity of air may be injected with a quantity of serum. To avoid this possibility, the inoculator 10 should be operated a number of times, each time a new ampule 40 is inserted into the same. Operation of the aforedescribed loaded inoculator is accomplished rather simply.

When the loading operation is completed and the inoculator 10 is rotated upward again about the axis 94 so as to cause it to be released from its engagement with the cocking balls 84 that fit into the recesses 126, the sear block 58 is then permitted to move back into engagement with the abutting surfaces of the locking notched end 62 of the trigger 64. When in such condition, the inoculator is ready to dispense serum from the injector head 132 and the chamber 140.

The dispensing or ejection of serum from the inoculator 10 is performed by the operator pressing the trigger 64 to cause it to rotate about its pin 66, thereby releasing the engagement of the notch 62 with the sear block 58. When the sear block 58 is freed by the pivoted trigger, it moves rapidly under the impetus of the main drive spring 72 toward the left to cause the main shaft 50 and the piston 18 to eject quickly the serum from the chamber 140 and passages 138 and 166. This sudden application of pressure applied by the piston 18 causes the serum in the injector head 132 and about the valve 152 to apply a force against the valve in opposition to the normally closing spring 154 to lift the valve against such spring and to lift the valve head from its seat 150, as shown in FIG. 6B, thereby permitting the serum fluid to be ejected forcefully outward from the injector head 132 at the orifice opening 148.

The amount of serum fluid to be injected during the operation just described may be variably controlled. Since it is necessary at times to control the volume of serum fluid to be dispensed by the inoculator 10, the same is provided with an adjusting means in the form of the dosage adjustment barrel 98. To accomplish the adjustment of the dosage ejected by the inoculator 10, the barrel 98 is threaded either to the left or to the right along the cocking barrel 78 toward and away from the retainer ring 74.

It will be recognized by those skilled in the art that when the barrel 98 is moved closer to the retainer ring 74, the space therebetween is reduced. When it is moved further away from the retainer ring 74, the space therebetween is increased. By reducing the space, the dosage ejected by the inoculator 10 may be decreased. By increasing the space, the dosage may be increased. The reason for this is that as the trigger 64 is released, the main shaft 50 moves to the left toward the retainer 74. When the barrel 98 abuts the retainer 74, the forward relative movement of the main shaft 50 with respect to the retainer 74 is halted by the abutment of the barrel 98 with the retainer 74. Hence, the extent of movement of the piston 18 is controlled in turn by the length of movement afforded by the position of the barrel 98 with respect to the retainer 74.

In practice, it has been found that the injector head 132 may conveniently contain an orifice 146 having a particular shaped opening 148 and a specific adjustment of the spring 154 within the head 156. At times it may be desirable to vary the particular orifice used and also the adjustment controlling movement of the valve 152. Rahter than disassemble the head 132, it has been found in practice easier simply to unthread the angled extension 134 from the threaded surface 14 of the cyllnder 16 and to apply to the same a different or substitute injector head having the orifice and valve and spring adjustment desired to perform a different function. Thus, interchangeable heads may be used by the technician either for shallow penetration inoculations or perhaps deeper bursal penetrations.

To enable the changing of functions to be performed by the interchangeable heads, the same may be accomplished rather simply by providing the piston 18 with a socket opening at its leading end. To provide for this, the end of passage 22 on the edge of the piston 18 may be conveniently shaped to accommodate a standard Allen-head wrench, which may be inserted into the same so that the piston 18 may be unthreaded at 52 from the main shaft 50.

This can be accomplished by first unthreading the head 132 from the main shaft 50 by rotating it off of the cylinder 16 at thread 14. Thereafter, the cylinder 16 may be unthreaded from the interior of the main shaft 50, thereby affording access to the Allen-type socket of the piston 18. The insertion of an Allen-head wrench into the socket enables the piston 18 to be unthreaded from the main shaft 50.

To change the head 132 to a completely different head 132' as shown in FIG. 7 having a different function, a new cylinder 16' may be threaded into the main body 12. This cylinder 16' may have a different internal diameter 140'. Thus, in the embodiment illustrated in FIG. 1, the cylinder interior diameter 140 may be used for the purpose of inoculation. That is to say, its interior diameter is relatively large, permitting the ejection of a large volume of fluid along the cylinder at low pressure by the piston 18. When the cylinder interior diameter 140' is reduced, obviously the volume of fluid to be pressurized therein is smaller and thus, the fluid will be placed under a higher pressure with the inoculator construction which remains as it has been disclosed above. Because the ejected fluid will be moved out of the smaller diameter cylinder 16' at higher pressure, the fluid will then penetrate the body tissues to a deeper extent.

To accomplish this, a new piston 18' may be rethreaded into the main shaft 50 in place of the original piston 18. The new piston 18' will mate with the interior diameter of the new cylinder 16' to move reciprocally therewithin. The new head 132' will replace the head 132 shown in the drawing. The new head 132' may be provided with a different orifice 148' to accomplish the intended function of the revised construction.

Figures 7, 8:
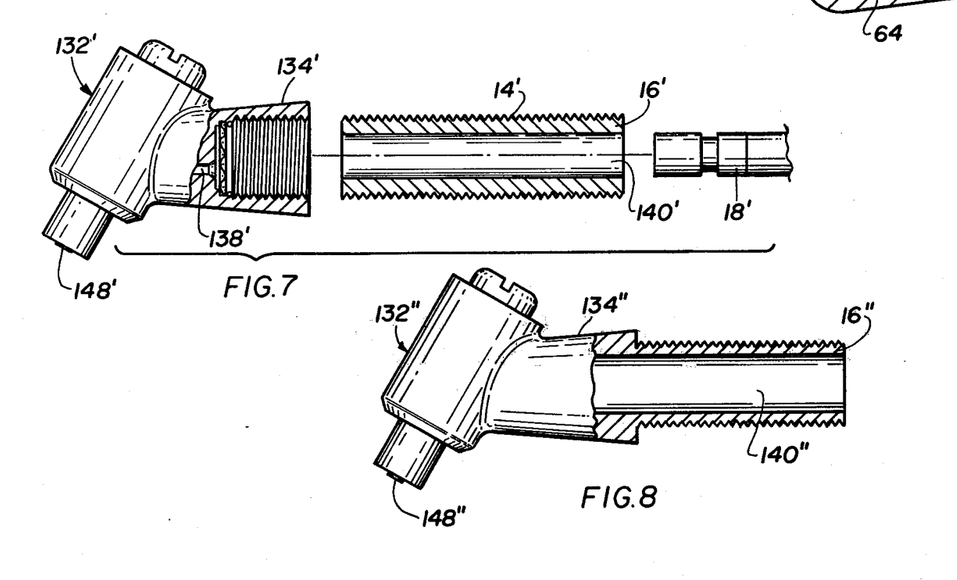
FIG. 7 is an exploded cross-sectional view of the interconnection of an injector head with the main body.
FIG. 8 is a cross-sectional view of another embodiment of the injector head and showing the details of its interconnection with the main body.

Those skilled in the art will recognize that it is within the scope of the present invention to include the cylinder 16" as a unitary extension of the angled extension 134" of the head 132", as shown in FIG. 8, so that when it is desired to remove the head 132" and the cylinder 16" from within the main body 12, both of them may be removed from the main body 12. In like manner, when it is desired to rethread a new head 132" and a new cylinder 16" into the main body 12, the unitary construction of the cylinder 16" with the angled extension 134" will enable this to be accomplished in one threading and unthreading step.

From what has been said, it will be apparent that the present invention is unusually simple in construction. The one-piece main body prevents any possible misalignment of connecting parts. The ability to purge the inoculator 10 during each loading action by causing the loading operation to exceed that movement necessary to put the sear block 58 into engagement with the notched end 62 of the trigger 64 and then permitting the main shaft 50 to return to a position whereby further movement to the left is prevented by engagement of the sear block 58 with the trigger notched end 62, assures that air will be completely purged from the system. The ability to adjust the barrel 98 to control the volume of fluid serum to be dispensed by the present inoculator is also a unique factor that makes this invention adaptable for multiple purposes quickly and easily.

Those skilled in the art will also recognize that the present invention is not restricted to the use of any one particular length of ampule 40. Rather, because of the various threaded adjustments between the cocking barrel 78 and the main shaft 50, and also between the cap 104 and the ampule drive body 102, it is possible to adjust these structures to accommodate longer or shorter serum-containing ampules.

Figures 1, 2:
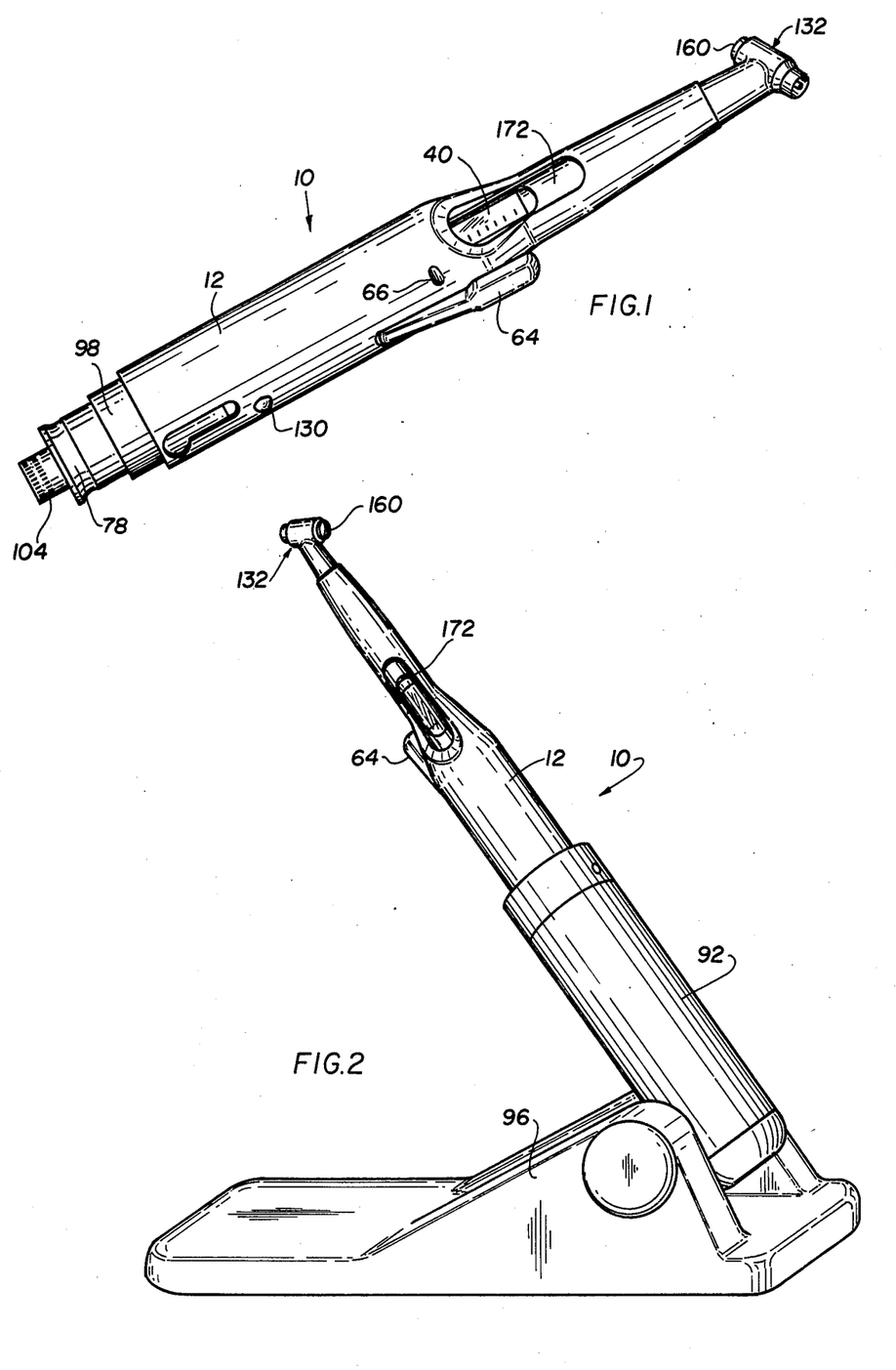
FIG. 1 is an elevational view illustrating the structure of an inoculator constructed according to the invention.
FIG. 2 is a perspective view of the inoculator of FIG. 1 mounted in the corking housing.

In practice, it has been found that a viewing opening may be provided in the barrel to enable the operator to see the contents of the ampule 40 through the barrel. This feature is more clearly illustrated in the drawing in FIGS. 1 and 2 and is identified by the numeral 172.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:
1. An inoculator apparatus comprising:
injector head means for containing a fluid to be ejected thereby,
an elongated body connecting with said injector head and defining a serum chamber of predetermined volume in fluid communication with said injector head,
an elongated unitary main shaft carrying at one end thereof a piston disposed in said serum chamber, said main shaft being movable in said body between charged and discharged positions and having an axially disposed opening for supporting a fluid containing ampule therein and for movement therewith and in fluid communication with said serum chamber,
operable means releasable from engagement with said main shaft to expose said opening to enable the insertion of a fluid containing ampule in said supporting opening and for applying a force to the fluid in an ampule contained in said supporting opening to enable the ejection of the fluid from the ampule into said serum chamber and said injector head as said main shaft moves from the discharged to the charged position,
cocking means normally relatively fixed with respect to said main shaft at an end thereof opposite said piston for moving said main shaft to its charged position,
said cocking means being operable to move said main shaft beyond its charged position to expand said serum chamber initially beyond its predetermined volume and to enable said main shaft to return to its cocked position and said serum chamber to its predetermined volume to purge said serum chamber of air,
adjustable means on and movable relative to said cocking member and to said body for engagement with said body when said main shaft is moved to its discharged position,
said adjustable means thereby being adjusted to limit the relative discharge movement of said main shaft with respect to said body and to selectively control the amount of fluid to be ejected by the inoculator,
trigger means on said body intermediate said cocking means and said piston to retain said main shaft in its charged position and to release the same for movement to its discharged position,
and energy storing means operable between said body and said main shaft for storing energy when said main shaft is moved to said charged position and to release its stored energy to move said main shaft to its discharged position.

2. The inoculator of claim 1,
said energy storing means being spring means.

3. The inoculator of claim 2,
said spring means being a spiral spring having square convolutions such that selected ones of said convolutions provide predetermined energy storing characteristics.

4. The inoculator of claim 1,
further comprising means adjustably cooperative with said cocking means to adjust the extent of the operation thereof to control the cocking movement of said main shaft.

5. An inoculator apparatus comprising:
injector head means for containing a fluid to be ejected thereby,
an elongated body connecting with said injector head and defining a serum chamber in fluid communication with said injector head,
an elongated unitary main shaft carrying at one end thereof a piston disposed in said serum chamber, said main shaft being movable in said body between charged and discharged positions and having an axially disposed opening for supporting a fluid containing ampule therein and for movement therewith and in fluid communication with said serum chamber, operable means releasable from engagement with said main shaft to expose said opening to enable the insertion of a fluid containing ampule in said supporting opening and for applying a force to the fluid in an ampule contained in said supporting opening to enable the ejection of the fluid from the ampule into said serum chamber and said injector head as said main shaft moves from the discharged to the charged position, cocking means normally relatively fixed with respect to said main shaft at an end thereof opposite said piston for moving said main shaft to its charged position, adjustable means on and movable relative to said cocking member and to said body for engagement with said body when said main shaft is moved to its discharged position, said adjustable means thereby being adjusted to limit the relative discharge movement of said main shaft with respect to said body and to selectively control the amount of fluid to be ejected by the inoculator, trigger means on said body intermediate said cocking means and said piston to retain said main shaft in its charged position and to release the same for movement to its discharged position, and energy storing means operable between said body and said main shaft for storing energy when said main shaft is moved to said charged position and to release its stored energy to move said main shaft to its discharged position, said operable means comprising sleeve means disposed in said chamber and releasably engaged with said main shaft for movement therewith between charged and discharged positions, elongated pusher means relatively movably connected with said sleeve means in said chamber and having an axial passage defined therethrough and an end closure member for engagement with a wall portion of an ampule contained in said supporting opening thereby to apply a force to the fluid in the ampule, cap means on said sleeve means for closing said supporting opening, and spring means between said cap means and said end closure member for normally urging said pusher means closure member into engagement with a wall portion of a supported ampule.

6. A method of purging an inoculator according to claim 1 of air therein, comprising the steps of:

providing said serum chamber in the inoculator in liquid communication with a serum containing ampule that is contained within the inoculator for receiving serum from the serum containing ampule, applying a force to a movable wall in the ampule to cause serum to flow from the ampule into the serum chamber, enlarging the serum chamber to a predetermined size to draw serum into the chamber from the ampule contained within the inoculator and fill the serum chamber from the ampule, enlarging the serum chamber greater than the predetermined size to further fill the same with serum from the ampule, and reducing the serum chamber to the predetermined size to increase the pressure on the serum in the chamber and cause the discharge therefrom of air trapped in the chamber prior to ejection of serum therefrom.

7. The method of claim 6, further comprising the steps of:

storing energy as the serum chamber is enlarged to and beyond the predetermined size, and partially releasing the stored energy to reduce the serum chamber to the predetermined size to purge the inoculator of air and prepare the same for inoculation.

8. The method of claim 6, further comprising the step of adjustably limiting the maximum enlargement of the serum chamber beyond its predetermined size during the enlargement thereof.

* * * * *